United States Patent [19]
Gittos et al.

[11] Patent Number: 5,910,501
[45] Date of Patent: *Jun. 8, 1999

[54] USE OF CERTAIN ESTERS OF HEXAHYDRO-8-HYDROXY-2,6-METHANO-2H-QUINOLOZIN-3(4H)-ONE AND RELATED COMPOUNDS FOR TREATING COGNITIVE DISORDERS

[75] Inventors: Maurice W. Gittos, Plobsheim; Marcel Hibert, Eschau, both of France

[73] Assignee: Merrell Pharmaceuticals Inc., Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/921,956

[22] Filed: Aug. 26, 1997

Related U.S. Application Data

[63] Continuation of application No. 08/772,186, Dec. 19, 1996, abandoned, which is a continuation of application No. 08/582,035, Jan. 2, 1996, abandoned, which is a continuation of application No. 08/437,244, May 8, 1995, abandoned, which is a continuation of application No. 08/309,568, Sep. 20, 1994, abandoned, which is a continuation of application No. 08/151,479, Nov. 12, 1993, abandoned, which is a continuation of application No. 08/046,108, Apr. 9, 1993, abandoned, which is a continuation of application No. 07/918,911, Jul. 23, 1992, abandoned, which is a continuation of application No. 07/806,987, Dec. 13, 1991, abandoned.

[30] Foreign Application Priority Data

Dec. 21, 1990 [EP] European Pat. Off. .............. 90403748

[51] Int. Cl.$^6$ .................................................... A61K 31/44

[52] U.S. Cl. ................................................................ 514/294
[58] Field of Search ............................................. 514/294

[56] References Cited

U.S. PATENT DOCUMENTS

| 4,845,115 | 7/1989 | Tyers | 514/397 |
|---|---|---|---|
| 4,906,755 | 3/1990 | Gittos | 544/126 |

FOREIGN PATENT DOCUMENTS

| 0190920 | 2/1986 | European Pat. Off. . |
| 0279990 | 12/1987 | European Pat. Off. . |
| 0342558 | 5/1989 | European Pat. Off. . |
| 0357415 | 8/1989 | European Pat. Off. . |
| 2231265 | 7/1987 | United Kingdom . |
| 2193633 | 2/1988 | United Kingdom . |

OTHER PUBLICATIONS

Barnes, et al., Pharmacology Biochem. & Behavior, vol. 35, 955–962 (1990).

Barnes, et al., Neuropharmacology, vol. 29 (11), 1037–1045 (Nov. 1990).

Neuropharmacology, vol. 29, No. 11, Nov. 1990, pp. 1,0237–1,045, Characterisation and Autoradiographic Localisation of 5–HT$_3$ Receptor Recognition Sites Identified with [$^3$H]–(s)–Aacopride in the Forebrain of the Rat.

*Primary Examiner*—Raymond Henley, III
*Attorney, Agent, or Firm*—Balaram Gupta

[57] ABSTRACT

This invention relates to the manufacture of certain esters of hexahydro-8-hydroxy-2,6-methano-2H-quinolizin-3(4H)-one and hexahydro-8-hydroxy-2,6-methano-2H-quinolizines and their use as medicaments in the treatment of cognitive disorders.

4 Claims, No Drawings

USE OF CERTAIN ESTERS OF HEXAHYDRO-8-HYDROXY-2,6-METHANO-2H-QUINOLOZIN-3(4H)-ONE AND RELATED COMPOUNDS FOR TREATING COGNITIVE DISORDERS

CROSS-REFERENCE TO RELATED APPLICATION

This is a continuation, of application Ser. No. 08/772,186, filed Dec. 19, 1996, now abandoned, which is a continuation of application Ser. No. 08/582,035, filed Jan. 2, 1996, now abandoned, which is a continuation of application Ser. No. 08/437,244, filed May 8, 1995, now abandoned, which is a continuation of application Ser No. 08/309,568 filed Sep. 20, 1994, now abandoned, which is a continuation of application Ser. No. 08/151,479, filed Nov. 12, 1993, now abandoned, which is a continuation of application Ser. No. 08/046,108, filed Apr. 9, 1993, now abandoned, which is a continuation of application Ser. No. 07/918,911, filed Jul. 23, 1992, now abandoned, which is a continuation of application Ser. No. 07/806,987, filed Dec. 13, 1991, now abandoned, which are herein incorporated by reference.

This invention relates to the manufacture of certain esters of hexahydro-8-hydroxy-2,6-methano-2H-quinolizin-3(4H)-one and hexahydro-8-hydroxy-2,6-methano-2H-quinolizines and their use as medicaments in the treatment of cognitive disorders.

More specifically, this invention relates to the use in the manufacture of a medicament for treating cognitive disorders utilizing compounds of the formula

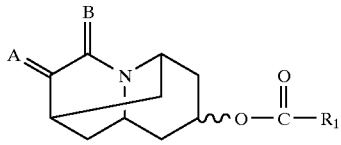

(1)

wherein A is $=H_2$, $=O$, $=(H)(OH)$ or $=N-OH$; B is $=H_2$, $=(H)(CH_3)$, $=(H)(CH_2NR_3R_4)$ or $=CH_2$ wherein $R_3$ and $R_4$ are $C_{2-4}$ alkyl or are combined to give tetramethylene, pentamethylene or $-CH_2-CH_2-O-CH_2CH_2-$;

$R_1$ is

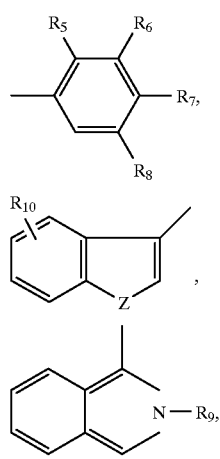

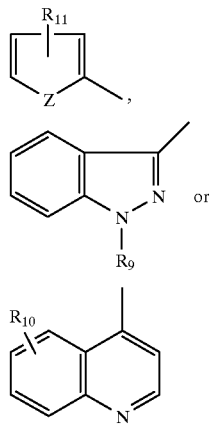

wherein Z is $NR_9$, O or S; $R_5$, $R_6$ and $R_8$ are each hydrogen, halogen, $C_{1-3}$ alkyl or $C_{1-3}$ alkoxy; $R_7$ is hydrogen, amino, $(C_{1-4}$ alkyl)amino, $(C_{1-4}$ alkyl)$_2$ amino, $C_{1-3}$ alkoxy or nitro; $R_9$ is hydrogen, $C_{1-4}$ alkyl or phenyl ($C_{1-2}$ alkyl); $R_{10}$ is hydrogen, halogen, $C_{1-4}$ alkyl, $C_{1-4}$ alkoxy, hydroxy, cyano or $-CONH_2$; $R_{11}$ is hydrogen, halogen, $C_{1-4}$ alkyl or phenyl; the wavy line indicates that the configuration of the oxygen substituent on the ring can be endo or exo; and the pharmaceutically acceptable acid addition and quaternary ammonium salts thereof.

Examples of the $C_{1-4}$ alkyl groups referred to above are methyl, ethyl, propyl, isopropyl and butyl. Examples of the $C_{1-4}$ alkoxy groups are methoxy, ethoxy and propoxy, with butoxy being an additional example when the alkoxy is $C_{1-4}$. The halogens referred to above can be fluorine, chlorine or bromine. When the wavy line in the general structural formula (1) is changed to a solid line, this indicates that the configuration of the compounds is endo. Such endo-compounds can also be referred to as trans. Similarly, exo-compounds can also be referred to as cis. Any hydrates of the present compounds are considered as equivalent to the compounds themselves and this would include compounds in which the carbonyl (i.e., A is $=O$) exists as $=(OH)_2$.

A preferred group of compounds are those wherein the ester is attached to the polycyclic ring in the endo-configuration. A further preferred group are those having the endo-configuration wherein A is $=O$ and $=(OH)_2$. In a still further preferred group, B is additionally $=H_2$.

The pharmaceutically acceptable acid addition salts referred to above can be non-toxic salts with suitable acids such as those with inorganic acids, for example, hydrochloric, hydrobromic, nitric, sulfuric or phosphoric acids; or with organic acids such as organic carboxylic acids, for example, acetic, propionic, glycolic, maleic, hydroxymaleic, malic, tartaric, citric, salicylic, 2-acetyloxybenzoic, nicotinic or isonicotinic; or organic sulfonic acids, for example, methanesulfonic, ethanesulfonic, 2-hydroxyethane-sulfonic, 4-toluenesulfonic or 2-naphtalenesulfonic. Quaternary ammonium salts are formed with alkyl halides such as methyl chloride, methyl bromide, methyl iodide or ethyl bromide; or with sulfate esters such as methyl 4-toluenesulfonate or methyl 2-naphthalenesulfonate.

As disclosed in U.S. Pat. No. 4,906,755, the compounds of the present invention can be prepared by reacting an alcohol or a reactive derivative thereof, said alcohol (2) having the formula

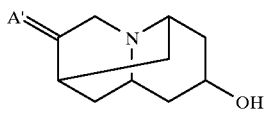

(2)

wherein A' is =O or =H$_2$, with a reactive equivalent of an acid (3) of the formula

R$_1$COOH　　　　(3)

wherein R$_1$ is defined as above. By a reactive equivalent of the acid is meant the corresponding acid chloride or bromide or the corresponding glyoxylyl chloride or bromide or the carboxylic acid imidazole obtained by the reaction of the appropriate acid halide with N,N-carbonyldiimidazole; or any similar acid derivative which would yield the simple carboxylic acid ester on reaction with an alcohol or with a reactive derivative of an alcohol. More specifically, where the -OH in the alcohol is equatorial (exo), then it can be reacted with the appropriate carboxylic acid imidazole obtained by the reaction of the acid halide with N,N-carbonyldiimidazole. Alternatively, the acid can be converted to the acid chloride by standard procedures (e.g., thionyl chloride) and then reacted with the alcohol or an alkali metal salt of the alcohol such as the lithium salt obtained by the reaction of lithium hydride with the alcohol in tetrahydrofuran.

When the —OH group in the starting alcohol is axial (endo), it can also be converted to the corresponding ester by reaction with the appropriate acid chloride or bromide with the reaction being carried out in the presence of an equivalent of a suitable tertiary base such as 4-dimethylaminopyridine in a high boiling inert solvent such as xylene. In the case, however, long heating (24–84 hours) at a temperature of or above 140° C. is necessary so that the procedure would not be suitable for use with acid halides that are not stable under the indicated conditions. Thus, it was necessary to use an alternative procedure for the preparation of such compounds. In this procedure, an appropriate acid chloride or bromide or a glyoxylyl chloride or bromide, in a nitroparaffin solvent, is reacted with a solution of a super acid salt (e.g., HBF$_4$) of the alcohol and an equivalent amount of a heavy metal salt (e.g., AgBF$_4$) of the same super acid. The glyoxylyl chloride can be used in the process as indicated because it decarbonylates readily under the conditions used. The reaction itself can be carried out over a period of 1–24 hours at temperatures ranging from –80° C. to ambient temperatures (about 23° C.). Examples of suitable super acids with M=H are MBF$_4$, MAsF$_6$, MSbF$_6$, MPF$_6$, MTaF$_6$, or MNbF$_6$ with examples of suitable heavy metals (M) being silver and thallium. Examples of nitroparaffin solvents are nitromethane, nitroethane, 1-nitropropane and 2-nitropropane.

In those instances, wherein the group R$_1$ contains a primary or secondary amino group, it is usually protected during the above reaction, with a benzyl group being commonly used to protect a secondary amine and a benzyloxycarbonyl group being used to protect a primary amine. In either case, the protecting group in the product is removed by conventional procedures, for example, by hydrogenation with hydrogen and a palladium catalyst.

Another alternative procedure is to react the alcohols of formula (2) with a mixed anhydride of trifluoroacetic acid and an appropriate carboxylic acid of formula (3). This process is particularly suitable for preparation of an indole-3-carboxylic acid ester of a hexahydro-8-hydroxy-2,6-methano-2H-quinolizin-3(4H)-one by reacting a 5-hydroxy-8-azatricyclo[5.3.1.0$^{3,8}$] undecan-10-one with the mixed anhydride of trifluoroacetic acid and the appropriate indole-3-carboxylic acid, said reaction taking place in an inert solvent at ambient temperatures in the presence of a tertiary amine.

Various procedures can be used to convert those compounds wherein A is =O and whose preparation is described below, to other different bridged derivatives of the present invention by standard methods. Thus, the ketone group in the polycyclic system can be reduced to the corresponding alcohol using an alkali metal (sodium or potassium) borohydride in a lower alkanol such as methanol or ethanol.

The ketone group can also be reduced completely to a methylene group by a two step procedure. In the first step, the ketone is reacted with ethylene dithiol or trimethylene dithiol in the presence of a strong acid such as hydrochloric acid or BF$_3$ to give the corresponding dithioketal. The reaction is carried out in a suitable polar solvent such as nitromethane or acetic acid. The dithioketal is then reduced with hydrazine in the presence of Raney nickel in a lower alkanol solvent such as 2-propanol at elevated temperatures (60–100° C.). Actually this same procedure can be used to reduce the original starting alcohol, hexahydro-8-hydroxy-2,6-methano-2H-quinolizin-3(4H)-one, to 8-hydroxy-2,6-methanooctahydro-2H-quinolizin which can itself be reacted with acid derivatives as described earlier to give the corresponding esters.

Compounds containing other B-groups (i.e. aminomethyl, methylene or methyl groups) can be obtained from products in which A is =O and B is =H$_2$ by a Mannich reaction using formaldehyde and a secondary amine such as dimethylamine, diethylamine, piperidine or pyrrolidine. This reaction gives the corresponding aminomethyl compound and, when B is dimethylaminomethyl, the amino moiety is eliminated on heating at 90–110° C. in an inert solvent such as toluene to give the corresponding methylene compound (B is =CH$_2$). This exocyclic methylene compound can be isolated by standard methods and transformed into a methyl group by hydrogenation, for example, by using hydrogen and platinum oxide.

To obtain those compounds in which A is hydroxyimino (=N—OH), the ketone referred to above can be reacted with hydroxylamine hydrochloride by standard procedures.

The alcohol used as a reactant in the above procedure can be obtained from known alkyl (C$_{1-4}$) 3-cyclopentene-1-carboxylates by a multi-step procedure. Specifically, the double bond in the indicated cyclopentene is oxidized to a 1,2-diol using N-methyl-morpholine N-oxide in the presence of osmium tetroxide catalyst. The diol is then cleaved to the corresponding dialdehyde using sodium metaperiodate. A Robinson-Schöpf cyclization of the dialdehyde with a lower alkyl glycine ester and acetone-dicarboxylic acid, preferably at pH4, gives a pseudopelletierine derivative (4) of the following type:

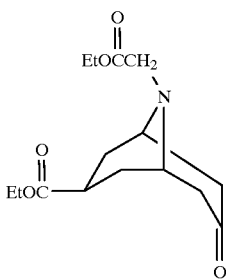 (4)

The ketone group is reduced to an alcohol using sodium borohydride and the product is reacted with dihydropyran to protect the —OH group as a tetrahydropyranyl ether. Dieckmann cyclization of the diester using a strong base (e.g., potassium t-butoxide) followed by aqueous acid hydrolysis and decarboxylation gives the desired alcohol. The resulting alcohols can exist in two conformations—axial and equatorial. The main product obtained by the above procedure is the axial alcohol and it can be separated from the equatorial isomer by crystallization of the camphorsulfonate or tetrafluoroborate salt.

Examples for the preparation of specific compounds of this invention may be found in U.S. Pat. No. 4,906,755, although the most preferred compounds of this invention are trans-hexahydro-8-(3-indolylcarbonyloxy)-2,6-methano-2H-quinolizin-3(4H)-one, preferably as the methanesulfonate (i.e., CAS-[115956-13-3]) or HCl salt and trans-hexahydro-8- (3-indolylcarbonyloxy)-2,6-methano-2H-quinolizin-3(4H)-ol as the methanesulfonate or HCl salt. Illustrative of compounds embraced by this invention are:

7-Ethoxycarbonyl-9-(ethoxycarbonylmethyl)-9-azabicyclo-[3.3.1]nonan-3-one;
7-Ethoxycarbonyl-9-(ethoxycarbonylmethyl)-9-azabicyclo-[3.3.1]nonan-3-ol;
Endo-hexahydro-8-hydroxy-2,6-methano-2H-quinolizin-3(4H)-one;
Endo-8-(3,5-dimethylbenzoyloxy)hexahydro-2,6-methano-2H-quinolizin-3(4H)-one;
Endo-hexahydro-8-(3-indolylcarbonyloxy)-2,6-methano-2H-quinolizin-3(4H)-one methanesulfonate melting at about 278° C.;
Endo-8-(3-benzofurancarbonyloxy)hexahydro-2,6-methano-2H-quinolizin-3(4H)-one;
Endo-8-(3-benzo[b]thiophenecarbonyloxy)hexahydro-2,6-methano-2H-quinolizin-3(4H)-one;
Endo-8-(l-benzyl-lH-indol-3-ylcarbonyloxy)hexahydro-2,6-methano-2H-quinolizin-3(4H)-one;
Endo-hexahydro-8-(1-methyl-lH-indol-3-ylcarbonyloxy)-2,6-methano-2H-quinolizin-3(4H)-one;
Endo-8-(4-bromo-2-furylcarbonyloxy)hexahydro-2,6-methano-2H-quinolizin-3(4H)-one;
Endo-hexahydro-8-(5-phenyl-2-furylcarbonyloxy)-2,6-methano-2H-quinolizin-3(4H)-one;
Endo-8-(3-chloro-2-thienylcarbonyloxy)hexahydro-2,6-methano-2H-quinolizin-3(4H)-one;
Endo-hexahydro-8-(5-methyl-2-thyenylcarbonyloxy)-2,6-methano-2H-quinolizin-3(4H)-one;
Endo-hexahydro-8-(1-methyl-lH-pyrrol-2-ylcarbonyloxy)-2,6-methano-2H-quinolizin-3(4H)-one;
Endo-8-(3-chloro-4-nitrobenzoyloxy)hexahydro-2,6-methano-2H-quinolizin-3(4H)-one;
Endo-8-(3-chloro-4-dimethylaminobenzoyloxy)hexahydro-2,6-methano-2H-quinolizin-3(4H)-one;
Endo-8-(3,5-dichlorobenzoyloxy)hexahydro-2,6-methano-2H-quinolizin-3(4H)-one;
Endo-8-(3,5-dimethoxybenzoyloxy)hexahydro-2,6-methano-2H-quinolizin-3(4H)-one;
Endo-8-(2,5-dimethylbenzoyloxy)hexahydro-2,6-methano-2H-quinolizin-3(4H)-one;
Exo-hexahydro-8-(3-indolylcarbonyloxy)-2,6-methano-2H-quino-lizin-3(4H)-one;
Endo-hexahydro-8-(5-methyl-3-indolylcarbonyloxy)-2,6-methano-2H-quinolizin-3(4H)-one hydrochloride;
Endo-hexahydro-8-(5-chloro-3-indolylcarbonyloxy)-2,6-methano-2H-quinolizin-3(4H)-one hydrochloride;
Endo-hexahydro-8-(5-carbomoyl-3-indolylcarbonyloxy)-2,6-methano-2H-quinolizin-3(4H)-one;
Endo-hexahydro-8-(5-hydroxy-3-indolylcarbonyl-oxy)-2,6-methano-2H-quinolizin-3(4H)-one;
Endo-hexahydro-8-(6-methyl-3-indolylcarbonyloxy)-2,6-methano-2H-quinolizin-3(4H)-one oxalate;
Endo-hexahydro-8-(1-methyl-3-indolylcarbonyloxy)-2,6-methano-2H-quinolizin-3(4H)-one hydrochloride;
Endo-hexahydro-8-(5-methoxy-3-indolylcarbonyloxy)-2,6-methano-2H-quinolizin-3(4H)-one hydrochloride;
Endo-hexahydro-8-(5-cyano-3-indolylcarbonyloxy)-2,6-methano-2H-quinolizin-3(4H)-one hydrochloride;
Endo-8-(3,5-dimethylbenzoyloxy)hexahydro-4-methyl-2,6-methano-2H-quinolizin-3(4H)-one tetrafluoroborate;
Endo-8-(3-indolylcarbonyloxy) -2, 6-methanooctahydro-2H-quinolizin;
Exo-8-(3, 5-dimethylbenzoyloxy)octahydro-2,6-methano-2H-quinolizin;
Endo-hexahydro-8-(1-methyl-3-indazolylcarbonyloxy)-2,6-methano-2H-quinolizin-3(4H)-one;
Endo-hexahydro-8-(3-indolylcarbonyloxy)-2,6-methano-5-methyl-3(4H)-oxo-2H-quinolizinium iodide;
Endo-hexahydro-8-(4-quinolinylcarbonyloxy)-2,6-methano-2H-quinolizin-3(4H)one hydrochloride;
Endo-8-(3-indolylcarbonyloxy)-2,6-methanooctahydro-2H-quinolizin-3-ol;
Trans-hexahydro-8-(3-indolylcarbonyloxy)-2,6-methano-2H-quinolizin-3(4H)-one methanesulphonate monohydrate.

Treatment of degenerative diseases of the brain and neurological impairments that result from stroke or serious head injuries has recently become an area of great interest and concern for the pharmaceutical and medical sciences. This interest has lead to a search for effective cognition enhancers for such diseases as Alzheimer's disease, other types of senile dementia, age associated memory impairment, attention deficits particularly in hyperactive children, and brain damage caused by stroke and brain injuries. Indeed, it is now established that these degenerative disease conditions are characterized by a selective loss in the cerebral cortex of choline acetyltransferase, the enzyme responsible for the synthesis of acetylcholine. There also exists a correlation between memory (or cognition) impairment or dementia and the decrement in cholinergic transmission. Thus cholinergic dysfunctions—or impairmed tranmission in the central nervous system may be, at least in part, responsible for the symptomatology of Alzheimer's disease and senile dementia. In support of these conclusions such compounds as physostigmine and 1,2,3,4-tetrahydro-9-aminoacridine (THA), compounds which prevent the catabolism of acetylcholine have found a place in the treatment of Alzheimer's and other senile degenerative diseases. Indeed, it has been recognized that the extent of improvement of cognitive functions has been closely related to the availability of acetylcholine. It is now believed that the compounds of this invention indirectly effect cognition enhancement and will therefore be useful in the treatment of degenerative diseases of the brain, e.g., Alzheimer's disease and senile dementia and will also be useful in treating neurological impairments resulting from stroke or head injuries.

The compounds of formula I are pharmacologically active agents capable of exerting $5HT_3$ antagonism as well as cognition enhancing effects as demonstrated by standard biological invitro and invivo test procedures, either alone or based upon comparative studies with agents known to have demonstrated such effects. One such procedure for demonstrating cognition enhancement effects is the Circular Maze assay. The circular maze paradigm is used as a measure of spatial memory in the rat and is based on that of Barnes (J. Comp. Physiol. Psychol. 1:74, 1979). The task requires an animal to escape from a circular test platform (1.2 M diameter) to a darkened "goal" box hidden under one of eighteen pre-designated areas located around the perimeter of the maze. The location of the goal box remains constant for each rat over trials but is randomized between rats.

Phase 1: Habituation: The rat is placed on the maze and allowed to explore for 2 minutes. If it does locate the goal box it is placed in it by the experimenter for 1 minute. The location of the box in this trial is different from that which is used in the following acquisition trials.

Phase 2: Six acquisition trials: The rat is placed in the centre of the maze under a black cylinder which is raised to begin the trial. The animal is allowed 4 minutes to locate the goal box. Its movements are recorded by an overhead camera linked to an image analysis system (Videotrack, Lyon Electronique, France).

Phase 3: Probe trial: The goal box is removed and the animal is allowed 2 minutes to explore the maze.

Two measures are used to evaluate mnemonic performance:

1. Latency to locate the goal box during the six acquisition trials. In control animals this latency decreases over the six trials.
2. Mean percentage entries into each of six pre-determined areas of the maze during the probe trial. These areas are (1) Training area: The area in which the goal box was formerly located during the acquisition trial; (2) Left+1: The area one unit to the left of the training area; (3) Left+2: The area two units to the left of the training area; (4) Right+1: The area one unit to the right of the training area; (5) Right+2: The area two units to the right of the training area; (6) Opposite: The area directly opposite to the training area.

Successful acquisition of the task in control animals produces a high percentage entries into the training area with percentage entries decreasing with increasing distance from the training area.

Administration of the muscarinic cholinergic antagonist scopolamine 0.5 mg/kg subcutaneously to rats 20 minutes prior to the test disrupts acquisition of the task as indexed by increased latency relative to controls and disruption of the characteristic pattern of percentage entries into the test areas during the probe trial. Compounds are evaluated against this scopolamine-induced disruption.

The effects of $5\text{-HT}_3$ antagonist 1H-indole-3-carboxylic acid, trans-octahydro-3-oxo-2,6-methano-2H-quinolizin-8-yl ester, methanesulfonate, monohydrate were evaluated against a deficit in acquisition of a spatial reference memory task in rats induced by the muscarinic cholinergic antagonist scopolamine (0.5 mg/kg). This procedure constitutes an animal model of a long-term spatial memory deficit consequent to central cholinergic dysfunction. Animals are trained to locate a goal box in a circular maze apparatus. Two parameters are measured: (1) latency to locate the goal box during six acquisition trials. Scopolamine (0.5 mg/kg) administered 20 minutes before training increases this latency compared to control animals treated with saline on three out of the six acquisition trials; (2) Search pattern during a 2 minute probe trial conducted 24 hours after the sixth acquisition trial during which no goal box is present. Control animals display a characteristic search pattern showing a greater percentage of entries into the location that formerly contained the goal box during the six acquisition trials, with the number of entries decreasing with increasing distance from this location. Scopolamine (0.5 mg/kg) disrupts this patters.

Animals treated with 1H-indole-3-carboxylic acid, trans-octahydro-3-oxo-2,6-methano-2H-quinolizin-8-yl ester, methanesulfonate, monohydrate alone (0.01, 0.1, 1.0 mg/kg) 15 minutes before training do not differ from control animals on either parameter. 1H-Indole-3-carboxylic acid, trans-octahydro-3-oxo-2,6-methano-2H-quinolizin-8-yl ester, methanesulfonate, mono-hydrate at 0.01 mg/kg and 0.1 mg/kg doses given 10 minutes after scopolamine significantly reversed the increase in latency on one out of the three trials impaired by scopolamine. At 1.0 mg/kg 1H-indole-3-carboxylic acid, trans-octahydro-3-oxo-2,6-methano-2H-quinolizin-8-yl ester, methanesulfonate, monohydrate reversed the scopolamine-induced increase on three out of three impaired trials.

1H-Indole-3-carboxylic acid, trans-octahydro-3-oxo-2,6-methano-2H-quinolizin-8-yl ester, methanesulfonate, monohydrate at 0.01 mg/kg and 1.0 mg/kg doses given 10 minutes after scopolamine restored search pattern during the probe trial to that of saline-treated control animals.

The present compounds can be administered in various manners to achieve the desired effect. The compounds can be administered alone or in the form of pharmaceutical preparations to the patient being treated either orally or parenterally, for example, subcutaneously or intravenously. They can also be administered by inhalation or by suppository. The amount of compound administered will vary and can be any effective cognition enhancing. Depending upon the patient and the mode of administration, the quantity of compound administered may vary over a wide range to provide from about 0.001 mg/kg to about 5 mg/kg, usually 0.01 to 3.0 mg/kg, of body weight of the patient per dose. Unit doses of these compounds can contain, for example, from about 0.5 mg to 100 mg, usually 1 to 50 mg and preferably 3 to 30 mg, of the compound and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In another aspect of this invention is the use of the compounds of Formula I in the manufacture of a medicament for treating cognitive disorders, particularly Alzheimer's disease and senile dementia, as well as those conditions such as brain damage caused by stroke and brain injuries.

Specific formulations of the present invention are prepared in a manner well known per se in the pharmaceutical art and usually comprise one or more active compounds of the invention in admixture or otherwise in association with a pharmaceutically acceptable carrier or diluent therefor. The active ingredient will usually be mixed with a carrier, or diluted by a diluent, or enclosed or encapsulated in a capsule, sachet, cachet, paper or other container. A carrier or diluent may be solid, semisolid or liquid material which serves as a vehicle, excipient or medium for the active ingredient. Suitable carriers or diluents are well known per se. See Remington's Pharmaceutical Sciences, Mack Publishing Company, Easton, Pa., for a description of the preparation of such formulations.

The formulations of the invention may be adapted for enteral or parenteral use and may be administered to the patient in the form of tablets, capsules, suppositories, solutions, suspensions or the like.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

What is claimed is:

1. The process for treating cognitive disorders which comprises administering to a patient in need thereof a therapeutically effective amount of a compound of the formula:

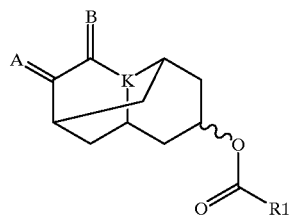

wherein the two lines to both A and B indicate a double bond to a single group or two single bonds to two individual groups as specified: A is (H) (H), =O, (H) (OH) or =N—OH; B is (H) (H), (H) (CH$_3$), (H) (CH$_2$NR$_3$R$_4$) or =CH$_2$ wherein R$_3$ and R$_4$ are C$_{2-4}$ alkyl or are combined to give tetramethylene, pentamethylene or —CH$_2$CH$_2$—O—CH$_2$CH$_2$—;

R$_1$ is

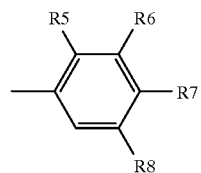

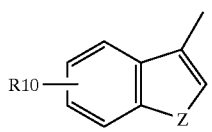

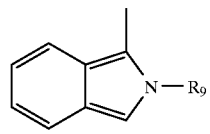

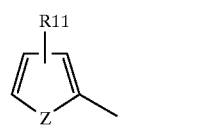

or

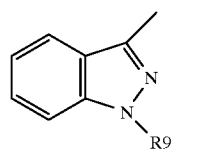

wherein Z is NR$_9$, O or S; R$_5$, R6 and R$_8$ are each hydrogen, halogen, C$_{1-3}$ alkyl or C$_{1-3}$ alkoxy; R$_7$ is hydrogen, amino, (C$_{1-4}$ alkyl)amino, (C$_{1-4}$ alkyl)$_2$ amino, C$_{1-3}$ alkoxy or nitro; R$_9$ is hydrogen, C$_{1-4}$ alkyl or phenyl(C$_{1-2}$ alkyl); R$_{10}$ is hydrogen, halogen, C$_{1-4}$ alkyl, C$_{1-4}$ alkoxy, hydroxy, cyano or -CONH$_2$; R$_{11}$ is hydrogen, halogen, C$_{1-4}$ alkyl or phenyl; the wavy line indicates that the configuration of the oxygen substituent on the ring can be endo or exo; and the pharmaceutically acceptable acid addition and quaternary ammonium salts thereof.

2. A process of claim 1 wherein the compound is trans-hexahydro-8-(3-indolylcarbonyloxy)-2,6-methano-2H-quinolizin-3(4H)-one, or trans-hexahydro-8-(3-indolyl-carbonyloxy)-2,6-methano-2H-quinolizin-3(4H)-ol.

3. A process of claim 1 wherein the cognitive disorder is Alzheimer's disease.

4. A process of claim 3 wherein the compound is trans-hexahydro-8-(3-indolylcarbonyloxy)-2,6-methano-2H-quinolizin-3(4H)-one, or trans-hexahydro-8-(3-indolyl-carbonyloxy)-2,6-methano-2H-quinolizin-3(4H)-ol.

* * * * *

UNITED STATES PATENT AND TRADEMARK OFFICE
CERTIFICATE OF CORRECTION

PATENT NO. : 5,910,501

DATED : June 8, 1999

INVENTOR(s) : Maurice Gittos and Marcel Herbert

It is certified that error appears in the above-identified patent and that said Letters Patent is hereby corrected as shown below:

Column 1, Line 11 reads as "filed December 19, 1996 and should read as --filed December 20, 1996--.

Column 6, Line 56 reads as "impairmed" and should read as --impaired--.

Column 7, Line 9 reads as "invitro and invivo" and should read as --*in vitro* and *in vivo*--.

Column 8, Line 16 reads as "patters" and should read as --pattern--.

Column 8, Line 21, reads as a part of paragraph "1H-Indole" and should read as new paragraph --1H-Indole--.

Signed and Sealed this

Tenth Day of April, 2001

*Attest:*

NICHOLAS P. GODICI

*Attesting Officer*   *Acting Director of the United States Patent and Trademark Office*